United States Patent [19]

Neumann et al.

[11] Patent Number: 5,338,771
[45] Date of Patent: Aug. 16, 1994

[54] JOINT ENDOPROSTHESIS WITH $Al_2O_3$ CERAMIC HEAD AND A COMPOSITE SOCKET AND PROCESS FOR MAKING IT

[75] Inventors: Gerd Neumann, Berlin; Peter Hutschenreuther, Stadtroda; Willfried Glien, Hermsdorf; Dagmar Raab; Barbara Leuner, both of Ilmenau; Gabriele Steinborn; Georg Berger, both of Berlin, all of Fed. Rep. of Germany

[73] Assignee: Eska Medical Luebeck Medizin Technik GmbH, Luebeck, Fed. Rep. of Germany

[21] Appl. No.: 852,228

[22] PCT Filed: Nov. 28, 1990

[86] PCT No.: PCT/DE90/00913

§ 371 Date: Jul. 28, 1992

§ 102(e) Date: Jul. 28, 1992

[87] PCT Pub. No.: WO91/08000

PCT Pub. Date: Jun. 13, 1991

[30] Foreign Application Priority Data

Nov. 28, 1989 [DD] German Democratic Rep. ... 334926

[51] Int. Cl.$^5$ .................. A61L 27/00; C08K 3/22
[52] U.S. Cl. ..................... 523/113; 523/115; 523/457; 524/436; 501/70; 501/109; 264/6; 623/18; 623/19; 623/20; 623/23
[58] Field of Search ............ 264/6; 523/113, 457, 523/115; 524/436; 623/18; 501/70, 109

[56] References Cited

U.S. PATENT DOCUMENTS

| | | | |
|---|---|---|---|
| 3,803,279 | 4/1974 | Bailey, Jr. et al. | 523/457 |
| 3,939,497 | 2/1976 | Heimke et al. | 3/1.912 |
| 4,652,534 | 3/1987 | Kasuga | 623/18 |
| 4,714,721 | 12/1987 | Franek et al. | 523/113 |
| 4,731,394 | 3/1988 | Vogel et al. | 523/115 |
| 4,969,910 | 11/1990 | Frey et al. | 623/22 |

FOREIGN PATENT DOCUMENTS

| | | |
|---|---|---|
| 0216016 | 4/1987 | European Pat. Off. |
| 0315795 | 5/1989 | European Pat. Off. |
| 2365022 | 6/1975 | Fed. Rep. of Germany |

OTHER PUBLICATIONS

Chemical Abstract Service Abstract No. 112:165028j for East German Patent No. DD 248,351, Sep. 1984.
English titles and abstracts for the following patents (written by Derwent): JP 57191252, EP 0315795/US 4969910, EP 0216016/US 4731394, DD 248351, DD 272603/DE 3917035, DE 2129832, DE 2305333 (English title only), and DE 2365022/US3939497.
P. Eyerer, Zeitschrift fuer Werkstofftechnik, 17, pp. 384–391, 422–428 and 444–448 (1986) untranslated Jul. 9, 1993.

Primary Examiner—Paul R. Michl
Assistant Examiner—Andrew E. C. Merriam
Attorney, Agent, or Firm—Panitch Schwarze Jacobs & Nadel

[57] ABSTRACT

A composite socket of a joint endoprosthesis may be fashioned in which the inorganic component of the socket has apatite and/or wollastonite crystalline phases and additionally secondary crystalline phases providing improved hydrolysis stability. The inorganic mixture consists (in mass % proportions) of 31–34% CaO, 10–12% $P_2O_5$, 43–46% $SiO_2$, 3–5% $Na_2O$, 2–3% $CaF_2$ and, beyond the 100% of the above components, also 0.5–11% $Al_2O_3$ and/or $Zr_2$ and $Al_2O_3$ or $TiO_2$ and $ZrO_2$ or $TiO_2$ and $ZrO_2$ and $Al_2O_3$, whereby the proportion of $TiO_2$ lies between 0.5 and 5%. Essential to the invention, too, is a certain grain size distribution and radius of aperture between the ball and the socket. The result is non-wearing operation of the endoprosthesis.

12 Claims, No Drawings

JOINT ENDOPROSTHESIS WITH AL$_2$O$_3$ CERAMIC HEAD AND A COMPOSITE SOCKET AND PROCESS FOR MAKING IT

FIELD OF THE INVENTION

The invention pertains to the use of glassy crystalline materials in the field of joint endoprosthetics by an elastic embedment of suitable ceramic bodies in physiologically harmless addition-polymerization synthetics in the socket, and by the minimization of frictional and abrasive forces through a combination with highly polished ceramic bodies in the ball, as well as by an optimal design of the sliding surfaces with respect to one another. The composite material thus serves as a sliding counterpart in artificial joints (e.g., hip, knee, elbow, shoulder, wrist and ankle joint prostheses, etc.) in which the other sliding counterpart consists of a molded body made of an Al$_2$O$_3$ ceramic. Prostheses such as these are used in various disciplines within bone replacement surgery, orthopedics and traumatology.

BACKGROUND OF THE INVENTION

Although progress has been made in the field of synthetic joint replacement by making one sliding counterpart consist of an Al$_2$O$_3$ ceramic and the other consist of a synthetic material, sufficient examples of prosthesis failures have become known.

The state of this technology which had been attained by approximately the year 1987 has been described by P. Eyerer (in Zeitschrift für Werkstofftechnik [Materials Technology Journal] 17 (1986), pp. 384–91, 422–28, 444–48).

DD-PS 272603 further explained the disadvantages of the various forms of polyethylene (e.g., PS-D 2129832), which have been used extensively until now. However, the same document also explained why one should not dispense with the damping effect of an organic polymer against shock loading (e.g., in a hip joint endoprosthesis). The use of a socket and joint head consisting of an Al$_2$O$_3$ ceramic thus becomes theoretically questionable (DE-PS 2305333).

To be specific, in the case of implants of bioinert materials based on ceramics, there is a large modulus difference between the implant and the bone. This often represents the cause of implant failure.

The associated failure mechanisms are attributable on one hand to undamped stress peaks at the sliding interface and the resulting pressure on one of the sliding counterparts, and on the other hand to constant local irritation in the osseous implant bearing and the resulting disintegration of the bone.

A composite material was therefore introduced as a solution to these problems. This composite material is based on a polyurethane or epoxy resin component and a filler material.

Patent specifications pertaining to this subject explain that materials of the CaO—P$_2$O$_5$—SiO$_2$ type with apatite and wollastonite crystal phases prove advantageous.

On the other hand, these very materials are known to possess excellent bioactive properties—that is, they form a direct bond with the bone (without connective tissue), as a result of their superior surface reactivity.

Although these substances are apparently also suitable for the manufacture of the composite material as a sliding counterpart in the interface between a composite and an Al$_2$O$_3$ ceramic, the surface reactivity itself is the justification for suspecting that the hydrolysis stability is inadequate for this application (without direct bone contact). Prevention of an implant failure caused by this insufficient hydrolysis stability is sufficient reason to search for a material which on one hand at least maintains (or even improves) the excellent sliding properties, and on the other hand clearly displays hydrolysis stability in comparison with known bioactive materials (e.g., DD 248351 A1, JP-P 57/191252).

The goal of the invention is to develop wear-resistant joint endoprostheses with long-term stability.

SUMMARY OF THE INVENTION

The invention is based on the task of improving the hydrolysis stability of known joint endoprostheses with a socket consisting of a polymer matrix containing an inorganic component with apatite and/or wollastonite crystal phases.

The task of the invention is accomplished by attaining a nonwearing operation of the convex portion of the artifical joint when a known Al$_2$O$_3$ ceramic with a highly polished surface is used as this convex part, by embedding high-strength mineral abrasion preventers in the bearing surface of the joint socket. This embedment is performed in such a manner that a great number of contact points between the frictional counterparts are formed by the mineral components from the very outset, and that the number of contact points remains as great as possible, even when the concave part of the artificial joint is subjected to deformational loading. The embedded abrasion preventers also possess a high affinity to the bed material, so that the frictional forces which occur can not loosen any particles from the bearing surface. In accordance with the invention, this is accomplished by optimizing the angle of aperture or the difference between the inner and outer ball on one hand, and on the other hand by optimizing the grain size distribution of the abrasion preventers.

In accordance with the invention, the composition of the glass ceramic material which forms the bearing surface of the socket varies as follows, with respect to these components (given in percent by mass):

| | |
|---|---|
| CaO | 31–34 |
| P$_2$O$_5$ | 10–12 |
| SiO$_2$ | 43–46 |
| Na$_2$O | 3–5 |
| MgO | 2–3.5 |
| CaF$_2$ | 3–5 |

Over and above the 100% of the above-mentioned components of the mixture, the glass ceramic material also constantly contains an additional 0.5 to 11% of Al$_2$O$_3$ and/or ZrO$_2$ or TiO$_2$ and Al$_2$O$_3$ or TiO$_2$ and ZrO$_2$ or TiO$_2$ and ZrO$_2$ and Al$_2$O$_3$; the TiO$_2$ can range from 0.5 to 5%.

In accordance with the invention, the specified difference between the inner radius of the socket and the outer radius of the head lies between 25 and 350 microns. This difference is essential to the invention because a so-called "breaking-in phase" (as occurs in the case of polyethylene sockets) does not occur in the endoprosthesis which is manufactured in accordance with the invention, and because this angle of aperture (or this difference) is fixed in advance. It is preferable for this difference to measure 30 to 300 microns. The socket and ball should approximate an ideal ball shape as closely as possible, i.e., radius deviations of more than 30 microns should not be tolerated.

It is also advantageous for the inorganic component to contain secondary crystal phases of 1 to 20%, selected from the group which includes feldspars, alpha-tricalciumphosphate, $CaTiSiO_5$ and zirconates. The quantity of the secondary crystal phases ideally amounts to 5-20%, and especially 8-15%.

Beyond the 100% of the mixture, a preferred composition of the organic component additionally contains 0.5-10% $ZrO_2$. Another preferred composition additionally contains 0.5-5% $TiO_2$ and $Al_2O_3$ and/or $ZrO_2$ up to a total of 10%. Another preferred composition additionally contains 0.5 to 10% $Al_2O_3$. One final preferred composition additionally contains 0.5-10% $ZrO_2$ and $Al_2O_3$.

A further object of the invention is a method for manufacturing a joint endoprosthesis with an $Al_2O_3$ ceramic head and a composite socket by fusion of an inorganic mixture, cooling and comminution of the crystalline material with apatite and/or wollastonite crystal phases, introduction into a polymer matrix and curing of the matrix in a socket shape. The process is characterized by the above-mentioned mixture composition, the above-mentioned grain size spectrum (which is distributed throughout the polymer matrix), and by the curing into a socket shape, the inner radius of which is maintained such that the subsequent combination with the $Al_2O_3$ ceramic head restricts the difference between inner socket radius and outer ball radius to a range of 25 to 350 microns.

DETAILED DESCRIPTION OF PREFERRED EMBODIMENTS

A polyurethane or an epoxy resin can be used as the polymer matrix. These are present in a proportion of 20 to 60% (by mass). When polyurethane is used, a polyfunctionality between 2.1 and 4.0—and especially between 3.3 and 3.6—is advantageous.

The total proportion of the functional groups in the polymers should be greater than or equal to 10%, and the glass temperature should lie above body temperature. The gelling time amounts to at least 3 minutes.

As far as the invention is concerned, it does not matter which process is used to manufacture the glassy crystalline material, i.e., it does not matter whether a glass ceramic, a ceramic, or a sintered glass ceramic is involved. Glass ceramic technology seems preferable as the manufacturing alternative which is most likely to guarantee that the goal of the invention will be attained, because of the slightly superior bending strength values for the nongranular material.

The presence of apatite and/or wollastonite is essential to the material in accordance with the invention. However, test results have even shown that secondary crystal phases—e.g., feldspars, alpha-tricalciumphosphate, $CaTiSiO_2$, various zirconates, etc.—are not only tolerable within a narrowly limited range, as was expected; rather, it was surprisingly determined that their presence can prove favorable up to a considerably large proportion.

Nonetheless, the proportion of secondary phases may not exceed a certain limit. The maximum proportion should therefore be less than or equal to 15% (by mass) when an additional secondary crystal phase is present in addition to the primary crystal phase. This maximum should be 20% when two or more secondary crystal phases are present. It is self-evident that the primary crystal phase (or phases) always forms a greater proportion than the secondary crystal phases.

In order to characterize another feature of the glassy crystalline material, a quick method of determining the chemical stability was applied.

The material to be studied is comminuted, and the grain size grouping which has been chosen for the determination (from 315 to 400 $\mu$m) is removed. The sample material is washed with ethanol and subsequently dried at 110° C. Ten samples of the substance to be studied, each weighing approximately 2 g, are determined on the analytical scale. Twice-distilled water is heated to 37° C. In each case, 200 ml of this water (as measured in a beaker) is mixed with the tared amount of approximately 2 g. This sample is covered with a beaker cover and kept standing in the incubator at 37° C. for 24 hours. After this period, the samples are transferred to filters which have previously been weighed. The beakers are then rinsed out with distilled water until no residue remains. The filters with the sample substance are then dried at 110° C. After cooling in the exsiccator, weighing is performed again to determine the weight loss, as follows: (initial weight in mg—final weight in mg) * 1000/initial weight in mg=result in mg of substance loss/g initial weight.

Part of the results determined by this method have been listed in table 1, together with data on the crystal phase determination and the chemical compositions of relevant materials, including comparative examples A and B.

It is apparent that the materials C and D described here exhibit a greater hydrolysis stability than some materials of the basic system $P_2O_5$—$CaO$—$SiO_2$.

The invention is further characterized by the fact that the grains with a size less than 10 $\mu$m make up a proportion less than 0.1% in the range of grain sizes of the ceramic material which is being used. The following procedure proves to be optimal:

After a grain size range of 50-500 $\mu$m (but more advantageously only 63-200 $\mu$m, and ideally only 100-200 $\mu$m) has been assembled, a glassy crystalline material undergoes preliminary drying at 150° C. in a thin layer. This grain size range should be composed as follows:

| | |
|---|---|
| 200 to 500 $\mu$m | 10% |
| 150 to 200 $\mu$m | 15-25% |
| 125 to 160 $\mu$m | 40-50% |
| 100 to 125 $\mu$m | 20-30% |
| 100 $\mu$m | 20% |

If the grain size range is selected more restrictively, there is a resulting increase in the proportion of the selected groupings; this was taken into account in the above-mentioned composition. The data reveal that this is not a particle sample with a normal distribution.

A proportion of 20 to 60% (of the total mass of the composite) is necessary for non-wearing operation of the artificial joint.

It was surprisingly found that by simply introducing coarsely crystalline, hard abrasion preventers (of the type characterized above) into a liquid resin mixture based on a suitable synthetic resin (which is formed by addition polymerization and meets the requirement of being physiologically harmless), and by pouring this crystal paste into an appropriate mold, it is possible to achieve an arrangement of the crystal surfaces at the surface of the resulting molded body which results in a minimum amount of wear.

In accordance with the invention, synthetics which are formed by addition polymerization (e.g., epoxy resins and polyurethane) may be considered especially suitable for the manufacture of molded materials used in medical technology, which are also described as biomaterials. The reason for this is that their manufacture requires no initiators, accelerators, plasticizers, stabilizers or similar additives which migrate later and are partially toxic. Furthermore, no solvent is involved in the processing in accordance with the invention. The manufacture of the polyurethane makes use of hydroxyl compounds of low molecular weight on one hand, such as trimethylolpropane, neopentyl glycol, 1,6-hexanediol, and 1,4-butanediol, as well as the polyols of higher molecular weight, such as polytetrahydrofuran, or monoricinoleates of the hydroxyl compounds with lower molecular weights.

95 to 105 equivalent-% of an aromatic, aliphatic or alicyclic diisocyanate is used as an addition component. Examples of these include familiar chemical compounds, such as hexamethylene diisocyanate, diphenylmethane - 4,4-diisocyanate, or a mixture of 2,4- and 2,6-toluene diisocyanate.

In order to guarantee the hydrolysis stability of the polymer matrix and to hold the abrasion preventers securely, it is important for the glass temperature of the casting resin which is used for the embedment to lie above the body temperature, and for the content of the functional groups which bring about a secure bond between the casting resin and the ceramic to amount to at least 10%.

In polyurethane, the urethane groups which are capable of forming hydrogen bonds act as the above-mentioned functional groups. In epoxy resins, the hydroxyl groups which are formed when polyamines are used as hardeners—or the ester groups which are formed when anhydrides are used—bring about interactions of the type described above.

In order to attain the required glass temperature of the polyurethane casting resins in accordance with the invention, the polyol functionality must be adjusted to between 2.1 and 4.0, and preferably between 3.3 and 3.6. For the same reason, it is also necessary to adjust the hydroxyl-equivalent weight of the polyol to between 100 g and 300 g of component/mol OH, and preferably between 150 g/mol and 200 g/mol.

In the case of epoxy resins, the glass temperature is attained by the use of known diglycidyl ethers of the aromatic diphenols, or by the use of isocyanuric acid triglycidyl ester, and by the use of phthalic anhydride, hexahydrophthalic anhydride and similar conventional epoxy resin hardeners. This manufacturing process—i.e., the technique of casting sockets, for example—yields significantly lower arithmetic mean roughness values and improved roundness results than is possible at all with the traditional manufacturing processes of machining and finishing.

In this way, it is possible to obtain joint endoprostheses consisting of one sliding counterpart made of an $Al_2O_3$ ceramic and a biocompatible composite material with great hydrolysis stability as the second sliding counterpart. These sliding counterparts provide especially non-wearing joints of high strength. Furthermore, the advantage of improved hydrolysis stability which is attained in this way minimizes the residual risk of using such joint prostheses, especially with regard to long-term use in the specialized field of human medicine. It was surprisingly determined that a very definite grain size spectrum for the "filler material" guarantees optimal sliding properties. This in turn is naturally a function of the material being used. The term "filler material" is misleading in the sense that it could lead one to mistakenly infer that no interactions occur between the organic polymers and the embedded material.

Provided along with the invention are materials which, although they are indeed chemically similar, are manufactured by different processes. On one hand, this is done in order to allow the selection of a cost-effective manufacturing method in each case, but on the other hand, to also allow the altering of properties (as necessitated by the process technology) to be selected according to the conditions. It thus becomes possible to apply appropriately adapted composites to specific areas of use, such as finger or hip joint prostheses. These differences in properties also have an effect on the overall properties, because interactions with the organic polymers occur.

Where the inorganic component of the composite is concerned, selections have been made from the full range of conceivable compositions of the basic system $P_2O_5$—$CaO$—$SiO_2$ with additives of $Al_2O_3$, $ZrO_2$ and $TiO_2$ which display especially great hydrolysis stability and with which the composite in the above-mentioned sliding interface does not lead to any wear which could impair function.

The invention is explained by means of the following examples.

SAMPLE EMBODIMENT

Examples 1 through 6 (A through F)

Mixtures in accordance with table 1 were fused and converted by means of conventional temperature conditions into ceramics, sintered glass ceramics, or glass ceramics.

TABLE 1

| | Examples of Glassy Crystalline Material | | | | | |
|---|---|---|---|---|---|---|
| | Composition Code | | | | | |
| Components | A | B | C | D | E | F |
| | Comparative Examples | | | | | |
| CaO | 31.9 | 31.9 | 31.9 | 31.9 | 31.9 | 31.9 |
| $P_2O_5$ | 11.2 | 11.2 | 11.2 | 11.2 | 11.2 | 11.2 |
| $SiO_2$ | 44.5 | 44.5 | 44.5 | 44.5 | 44.5 | 44.5 |
| $Na_2O$ | 4.6 | 4.6 | 4.6 | 4.6 | 4.6 | 4.6 |
| MgO | 2.8 | 2.8 | 2.8 | 2.8 | 2.8 | 2.8 |
| $CaF_2$ | 4.8 | 5.0 | 5.0 | 5.0 | 5.0 | 5.0 |
| $K_2O$ | 0.2 | — | — | — | — | — |
| $TiO_2$ | — | 10.0 | — | — | — | — |
| $ZrO_2$ | — | — | 1.0 | 8.0 | 10.0 | — |
| $Al_2O_3$ | — | — | 1.0 | 1.0 | — | 10.0 |
| Primary Crystal Phases | Ap Wo | Ap Wo | Ap Wo | Ap Wo | Ap Wo | Ap Wo |
| Secondary Crystal Phases | — | $CaTiSiO_5$ Rutile | Unidentifiable | | $CaZrSi_4O_{12}$ | Feldspars α-TCP |
| Quick Method [mg/g] | 2.27 ±0.8 | 2.26 ±0.3 | 1.80 ±0.2 | n. b. | 1.78 ±0.1 | 1.76 ±0.1 |

Legend:
Ap — apatite; Wo — wollastonite; TCP — tricalciumphosphate; n. b. — undetermined

EXAMPLE 7

20 g of a polyol mixture (which results from mixing a ricinoleic acid trimethylpropane ester with additional trimethylolpropane, and exhibits a hydroxyl-equivalent weight of 190 g ester/mol OH and a functionality of 3.0) is intimately mixed with 20 g of a glass ceramic granulate (described below) and dried. The polyol mixture displays a viscosity of 1000 mPa.s at 40° C. 10 g of distilled toluene diisocyanate (equivalent weight: 90 g/mol NCO) is added to this suspension, thus producing a mixture which is pourable at 40° C. and hardenable. By pouring into a mold with an upright hemispherical shape, and after curing at temperatures between 40° and 80° C., a cast socket can be removed from the mold. This socket's resistance to wear can then be tested.

A material with a chemical composition corresponding to example C was used as a glass ceramic biomaterial in the following grain size grouping, in order to form the composite:

| | |
|---|---|
| up to 200 μm | 17.7% |
| up to 160 μm | 42.6% |
| up to 125 μm | 22.6% |
| up to 100 μm | 6.8% |
| up to 90 μm | 8.5% |
| up to 71 μm | 1.3% |
| <63 μm | <0.1% |

The wear studies yielded the following results. A polyurethane of the composition described above combined with 40% bioceramic shows better wear behavior than PE in tests against $Al_2O_3$ ceramics, as shown by the summary table:

Summary Table for Wear Behavior

| | | $Al_2O_3$/ Socket in accordance with example 7 | $Al_2O_3$/ Socket in accordance with example 8 |
|---|---|---|---|
| | $Al_2O_3$/PE | | |
| 1. mg/abrasion | 95 | immeasurable | immeasurable |
| 2. arithmetic roughness, average in μm | 0.69 | 0.18 | 0.16 |
| 3. maximum roughness - average | 4.56 (8.82) X) | 2.16 (2.29) X) | 1.55 (2.00) X) |

X) Absolute maximum roughness
Measurement Conditions: smear tests with water at 37° C., 2000 N load, 2,000,000 load reversal, test frequency 1 Hertz, angle of traverse 45°

EXAMPLE 8

14 g of a crystalline epoxy resin based on isocyanuric acid is introduced into a process of addition polymerization with 20 g of freshly distilled hexahydrophthalic anhydride at 110° C. After a 20 minute prereaction, the mixture displays a viscosity of approximately 500 mPa.s. At this viscosity, 20 g of a selected glass ceramic biomaterial is stirred in, and the suspension is poured into the mold, which has been preheated to 100° C. After curing (24 hours at 110° C.), it is possible to remove a cast socket from the mold. This socket also possesses the wear properties shown in the summary table for example 7.

A material with a chemical composition corresponding to example C was used in the following grain size grouping, in order to form the composite:

| | |
|---|---|
| up to 200 μm | 21.0% |
| up to 160 μm | 48.2% |
| up to 125 μm | 25.3% |
| up to 100 μm | 6.4% |

The properties listed here demonstrate the suitability of the described composite material in accordance with the invention as a wear-resistant socket material for joint prostheses.

We claim:
1. A process for manufacturing a joint endoprosthesis having an $Al_2O_3$ ceramic head and a composite socket comprising the steps:
  (a) fusing an inorganic mixture of a first component mixture and a second component to form a ceramic, glass ceramic or sintered glass ceramic material having apatite and/or wollastonite crystal phases, wherein the first component mixture comprises, in percent by mass of the first component mixture,

| | |
|---|---|
| 31–34% | CaO |
| 10–12% | $P_2O_5$ |
| 43–46% | $SiO_2$ |
| 3–5% | $Na_2O$ |
| 2–3.5% | MgO |
| 3–5% | $CaF_2$ | and the second component comprises 0.5 to 11%, relative to the mass of the first component mixture, of a compound selected from the group consisting of $Al_2O_3$, $ZrO_2$, $TiO_2$ and mixtures thereof, with the proviso that $TiO_2$ be present in the inorganic mixture at no more than 5% of the first component mixture;
  (b) cooling and comminuting the ceramic material such that the comminuted ceramic material has a grain size distribution of:

| | |
|---|---|
| 200–500 microns | less than 10% |
| 160–200 microns | 15 to 25% |
| 125–160 microns | 40 to 50% |
| 100–125 microns | 20 to 30% |
| less than 100 microns | less than 20% |
| less than 10 microns | less than 0.1%; |

(c) introducing the comminuted ceramic material into a polymeric matrix comprising polyurethane or an epoxy resin to prepare a composite of ceramic material and matrix;
  (d) curing the composite resulting from step (c) to provide a composite socket; and
  (e) combining the composite socket with an $Al_2O_3$ ceramic head such that the difference between the radius of the socket and the radius of the head lies within the range of 25 to 350 microns, and the radius of the socket and the radius of the head deviate from an ideal spherical shape by 30 microns or less.

2. A process in accordance with claim 1, wherein the second component of the inorganic mixture comprises 0.5 to 10%, relative to the mass of the first component mixture, of a compound selected from the group consisting of $Al_2O_3$, $ZrO_2$ and $TiO_2$, with the proviso that $TiO_2$ be present in the inorganic mixture at no more than 5% of the first component mixture.

3. A process in accordance with claim 2, wherein the second component of the inorganic mixture comprises 0.5 to 5%, relative to the mass of the first component mixture, of $TiO_2$, in addition to at least one of $Al_2O_3$ and $ZrO_2$, for a total mass of up 10%, relative to the mass of the first component mixture.

4. A process in accordance with claim 2, wherein at least one of $Al_2O_3$ and $ZrO_2$ is present in the second component of the inorganic mixture, in similar or different proportions, within a range of 0.5 to 10% relative to the mass of the first component mixture.

5. A process in accordance with claim 1, wherein the polymeric matrix is formed by a polyurethane which is produced from at least one polyol and an aromatic, aliphatic or alicyclic di-isocyanate, and has a proportion of functional groups greater than or equal to 10%.

6. A process in accordance with claim 5, wherein the polymeric matrix has a glass transition temperature greater than body temperature.

7. A process in accordance with claim 5, wherein the polymeric matrix is a polyurethane having polyfunctionality between 2.1 and 4.0.

8. A process in accordance with claim 7, wherein the polyfunctionality of the polyurethane is between 3.3 and 3.6.

9. A process in accordance with claim 1, wherein the polymeric matrix is formed by an epoxy resin and a hardening agent, and has a proportion of functional groups greater than or equal to 10%.

10. A process in accordance with claim 9, wherein the polymeric matrix has a glass transition temperature greater than body temperature.

11. A process in accordance with any one of claims 1 through 26, wherein the comminuted ceramic material comprises 20 to 60% of the total mass of the composite material.

12. A process in accordance with claim 1, wherein the polymeric matrix has a gelling time of at least 3 minutes.

* * * * *